(12) United States Patent
Deguchi et al.

(10) Patent No.: US 7,135,111 B2
(45) Date of Patent: Nov. 14, 2006

(54) SEPARATION ANALYZER

(75) Inventors: Kisaburo Deguchi, Sapporo (JP); Shinya Ito, Hitachinaka (JP); Masahito Ito, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 455 days.

(21) Appl. No.: 10/776,263

(22) Filed: Feb. 12, 2004

(65) Prior Publication Data

US 2004/0178133 A1 Sep. 16, 2004

(30) Foreign Application Priority Data

Mar. 11, 2003 (JP) ............................. 2003-064319

(51) Int. Cl.
*B01D 15/08* (2006.01)
(52) U.S. Cl. .................... 210/198.2; 210/101; 210/143
(58) Field of Classification Search ................ 210/635, 210/656, 659, 101, 143, 198.2; 422/70
See application file for complete search history.

(56) References Cited

U.S. PATENT DOCUMENTS

| | | | |
|---|---|---|---|
| 4,158,630 A * | 6/1979 | Stearns ..................... | 210/198.2 |
| 4,352,780 A | 10/1982 | Schick | |
| 5,283,036 A | 2/1994 | Hofmann et al. | |
| 5,462,660 A | 10/1995 | Singleton et al. | |
| 5,935,443 A * | 8/1999 | Anderson et al. ........... | 210/656 |
| 5,958,227 A * | 9/1999 | Uematsu ................... | 210/198.2 |
| 5,968,367 A | 10/1999 | Quinn et al. | |
| 6,235,197 B1 * | 5/2001 | Anderson et al. ........... | 210/635 |
| 6,502,448 B1 * | 1/2003 | Rapkin ....................... | 73/1.03 |
| 6,942,793 B1 * | 9/2005 | Ito et al. ................... | 210/198.2 |
| 6,989,129 B1 * | 1/2006 | Licklider et al. ............. | 422/70 |
| 2005/0194318 A1 * | 9/2005 | Ozbal et al. ................ | 210/656 |

FOREIGN PATENT DOCUMENTS

| | | |
|---|---|---|
| DE | 40 18 928 A | 12/1991 |
| JP | 2002-71657 | 3/2002 |
| JP | 2002-365272 | 12/2002 |

OTHER PUBLICATIONS

"Gas-pressure-driven stepwise-gradient elution system for microcolumn liquid chromatography", Bunseki Kagaku, vol. 50, No. 12, pp. 825-828 (2001).

* cited by examiner

*Primary Examiner*—Ernest G. Therkorn
(74) *Attorney, Agent, or Firm*—Dickstein Shapiro LLP

(57) ABSTRACT

A separation analyzer for transferring solutions, while changing mixing ratios of the solutions, wherein a flow passage from a first pump, a flow passage from a second pump, and a passage for sample introduction section, the flow passages being connected, which further comprises a flow switching means for temporarily storing the solutions, whereby the flow switching means alternatively makes a first state for pushing out the solutions in a second sampling loop to the sample introduction section by the second pump, while transferring the solutions to the first sampling loop; and a second state for pushing out the solutions in the first sampling loop by the second pump, while transferring the solutions from the first pump to the second sampling loop.

7 Claims, 6 Drawing Sheets

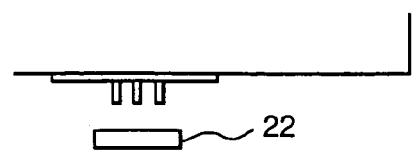
FIG. 6a
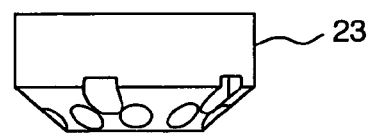
FIG. 6b
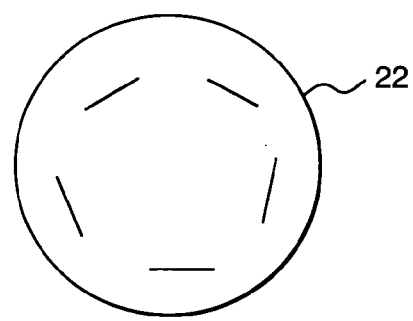
FIG. 6c
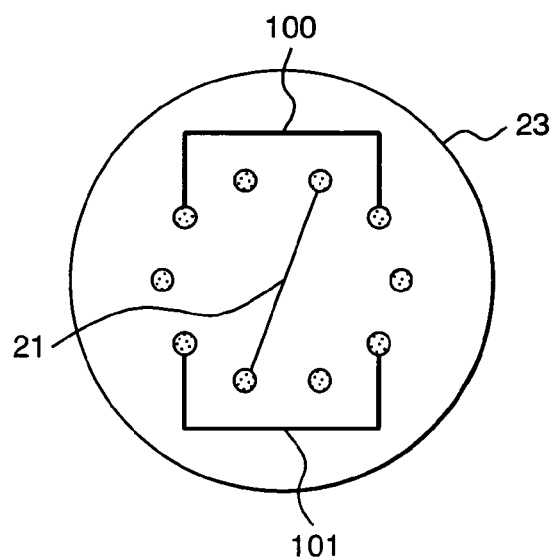

SEPARATION ANALYZER

DESCRIPTION OF THE INVENTION

1. Field of the Invention

The present invention relates to a separation analyzer, and more particularly to a separation analyzer for realizing gradient separation analysis at a rate of a nano-flow level (nL/min.).

In the specification of the present application, the term "gradient" is used to mean "preparation of divided solutions having different mixing ratios each other, the solutions being prepared by mixing plural kinds of solutions". Thus, the solutions for analysis have gradient concentrations as a whole.

2. Description of Related Prior Art

In carrying out analysis, while gradient eluting a sample at a flow rate of a nano-litter level (nL/min.), which uses separation analyzers, such as chromatographic analyzers, there are following several methods. One of them is a system wherein a nano-flow is obtained by splitting the solution into a splitting ratio of 1:100, for example, the solution being transferred from a pump with a low pressure or high pressure gradient function of a micro-flow. Another is a system wherein after a gradient solution that is required for one analysis is stored in one or several tubes or holes, and then the gradient solutions are introduced into separation columns using a solution transferring pump or a gas pressure vessel. (These systems are disclosed in the following patent documents 1, 2 and the non-patent document 1, etc.).

Patent Document 1: Japanese Patent Laid-open 2003-365272

Patent Document 2: Japanese Patent Laid-open 2002-71657

Non-patent Document 1: BUNSEKI KAGAKU, 50, 825 (2001)

In carrying out splitting the solution with the splitter mentioned-above, it is difficult to obtain a steady flow rate, because clogging of the flow passages takes place. Further, in filling gradient solutions that is required for one analysis in one or more tubes or holes, the filling of the solutions in one or more tubes or holes has to be done for each analysis. Therefore, it is impossible to carry out automatic analysis with high efficiency.

BRIEF DESCRIPTION OF THE DRAWINGS

FIGS. 6a to 6c show the construction of another improved ten-ports valve, wherein FIG. 6a is a development view of the ten-ports valve, FIG. 6b is a plane view of a rotor seal, and FIG. 6c is a plane view of a stator.

SUMMARY OF THE INVENTION

An object of the present invention is to solve the above-mentioned problems and to conduct separation analysis according to a gradient elution at a nano-flow level (nL/min.)

The feature of the present invention to solve the above-mentioned problems resides in a separation analyzer comprising a first pump for transferring liquid, while changing mixing ratios of plural kinds of solutions; a second pump for transferring a transfer solution; a sample introduction section; a separation column for separating a sample; and a detector for detecting the sample eluted from the separation column, wherein there is disposed a flow switching means having a first and second sampling loop for temporarily storing the solutions and comprising a flow passage from the first pump, a flow passage from the second pump and a flow passage from the sample introduction section, the passages being connected to each other, and wherein the flow switching means alternatively makes a first state where the second pump pushes out the solution in the second sample loop towards the sample introduction section, while transferring the solution from the first pump to the first sampling loop, and makes a second state where the second pump pushes out the solution in the first sampling loop, while transferring the solution from the first sampling loop to the second sampling loop.

As a result, even when gradient solutions are transferred from the first pump at a flow rate of a micro-flow level (µL/min.), the flow rate of the solutions can easily be changed to the amounts of the volumes transferred from the second pump by the flow switching means.

DESCRIPTION OF THE PREFERRED EMBODIMENTS

The embodiments of the present invention are explained in the following.

Figure 1:
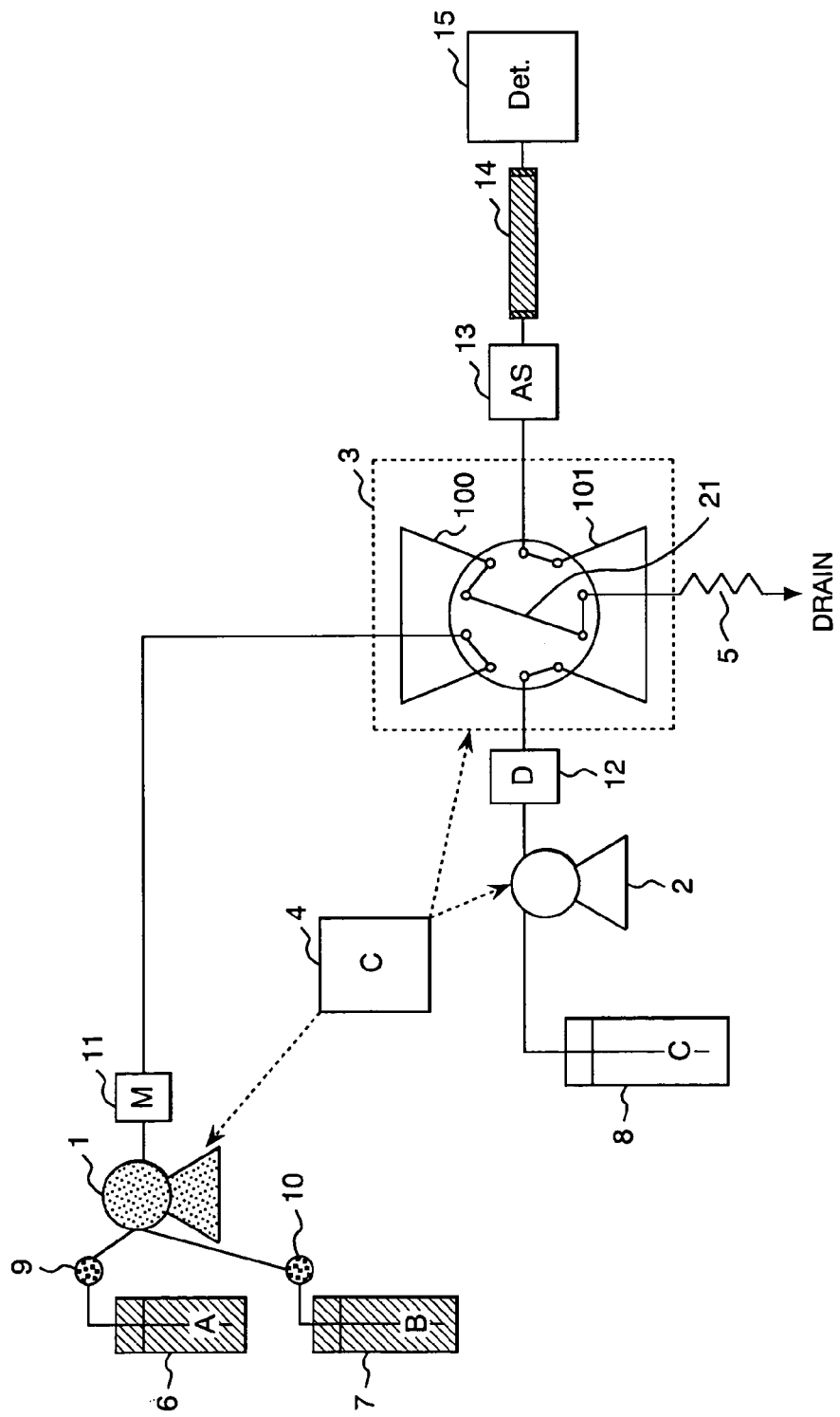
FIG. 1 is a diagrammatic drawing of an embodiment of the present invention.

In FIG. 1, a diagrammatic drawing of the present invention is shown. Pump 1 transfers two kinds of solutions 6, 7 at a rate of a micro flow level (µL L/min.) by the gradient system, wherein mixing ratios of the solutions are determined by ON/OFF operations of electromagnets (solenoid valves) 9, 10. In case of a high pressure gradient system, each of the solutions is provided with a solution transfer pump. The solutions provided by the pump 1 are mixed by a mixer 11, and then they are transferred to a ten-ports valve 3 (a valve having ten ports).

The ten-ports valve 3 is provided with sampling loops 100, 101, and the solutions supplied by the pump 1 is loaded on one of sampling loops 100 and 101 when the flow passages are switched. Each of the volumes of the sampling loops 100, 101 is about 1 micro litter, respectively. The flow passages to be switched are flow paths for communicating with the holes.

In the state shown in FIG. 1, the solution from the pump 1 constitutes a flow path comprising sampling loop 100, flow passage 21, and a drain via resistance coil 5 (or resistance column or pressure control valve). When the valve is switched, solution from the pump 1 constitutes a flow path comprising flow passage 21, sampling loop 101 and a drain via resistance coil 5.

The ten-ports valve 3 is connected with pump 2 (a syringe type or reciprocating type, for example) for transferring the solution 8 at a rate of a nano-flow level (nL/min.) via the damper 12. In the state shown in FIG. 1, there is formed a flow path that connects to the sample injector 13 for supplying solutions to the sample via the sampling loop 101. When the valve is switched, there is formed a flow path that is connected to the pump 2 and the sample injector 13 via the sampling loop 100.

After sample injector 13 injects the sample into the separation column 14, the sample is separated in the sample separation column 14, and the detector 15 detects the sample. As the detector 15, a UV-VIS photo-absorption detector, a luminescent detector, an electro-chemical detector, a mass-spectrometer analyzer, etc. can be used.

The controller 4 controls flow rates of the pumps 1, 2, gradient program, and periodical switching operation of valve 3. If pump 1 itself has a function for issuing relay signals, the controller 4 is not necessary, because the ten-ports valve 3 can be controlled by the pump 1.

The resistance coil 5 has a flow resistance, which is a pressure equivalent to that caused by the separation column 14. As a result, a pressure fluctuation that is caused by switching the ten-ports valve 3 can be made minimum. Further, the damper 12 at the lower flow of the pump 2 performs the similar advantage. The damper 12 has advantages such that pulsating flow stemmed from the pulse motor generated by the reciprocating valve or syringe type valve is eliminated.

Since the volume of the solution 8 supplied by the pump 2 is extraordinarily smaller than that from the pump 1, it does not actually arrive at the separation column 14. Accordingly, as the pump 2, an electro-osmotic flow pump can be used. When the solution is supplied at a constant flow rate, a gas pressure vessel can be used from the similar reason.

Figure 2:
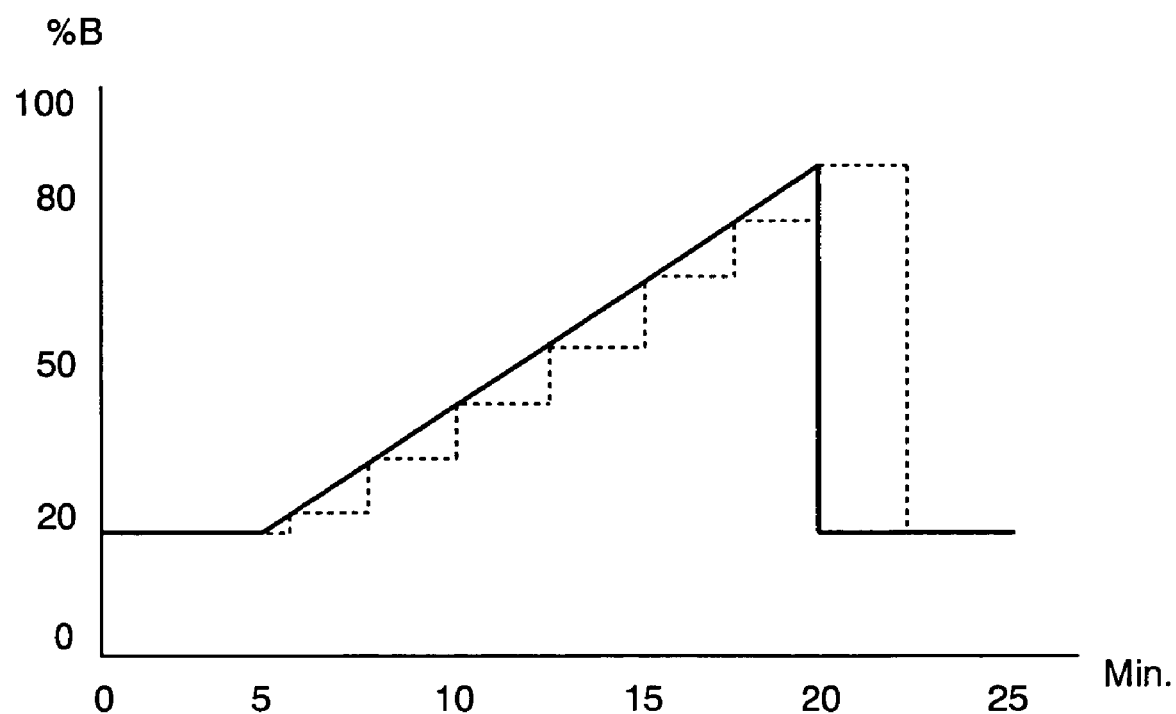
FIG. 2 is a drawing showing a gradient curve (continuous line) of a solution transferred by a pump 1 and a gradient curve (dotted line) of a solution transferred by the ten-ports valve.

FIG. 2 shows a diagram for explaining a gradient curve obtained in the constitution of FIG. 1. The gradient curve (continuous line) shows a solution supplied by the pump 1, and the gradient curve (dotted line) shows the solution after it passes the ten-ports valve 3.

Transfer of the solution from the ten-ports valve is performed by pushing out with the solution 8 that is transferred by the pump 2 at a rate of a nano-flow level (nL/min.). Although a volume of the sampling loop is the order of 1 µL as mentioned before, the flow rate of the solution from the pump 2 is only the nano-flow level (nL/min.) so that the solution 8 is not transferred to the sampling injector 13 beyond the sampling loop, even when the solution is transferred for several minutes. The solution 8 entered into the sampling loop is pushed into the drain by the action of the solution of a new composition and is discharged outside of the analyzer, when the ten-ports valve is switched.

In the constitution of FIG. 1, when the ten-ports valve is switched in every two minutes, the nano-flow low gradient curve (dotted line) of the solution at the lower flow of the ten-ports valve follows the gradient curve (continuous line) of the pump 1 in every two minutes. If switching of the ten-ports valve 3 is done in every one minute as shown in FIG. 2, the nano-gradient curve (dotted line) becomes a stepwise form in every one minute. The following property of the gradient curve (dotted line) to the former gradient curve (continuous line) becomes better by simply shortening the switching period(or interval) of the ten-ports valve.

The minimum time interval for valve switching is determined by the flow rate of pump 1 and a volume of the sampling loop. That is, it is calculated in accordance with the following equation. The minimum valve switching time interval=the volume of sampling loop/the flow rate of the pump 1

Figure 3:
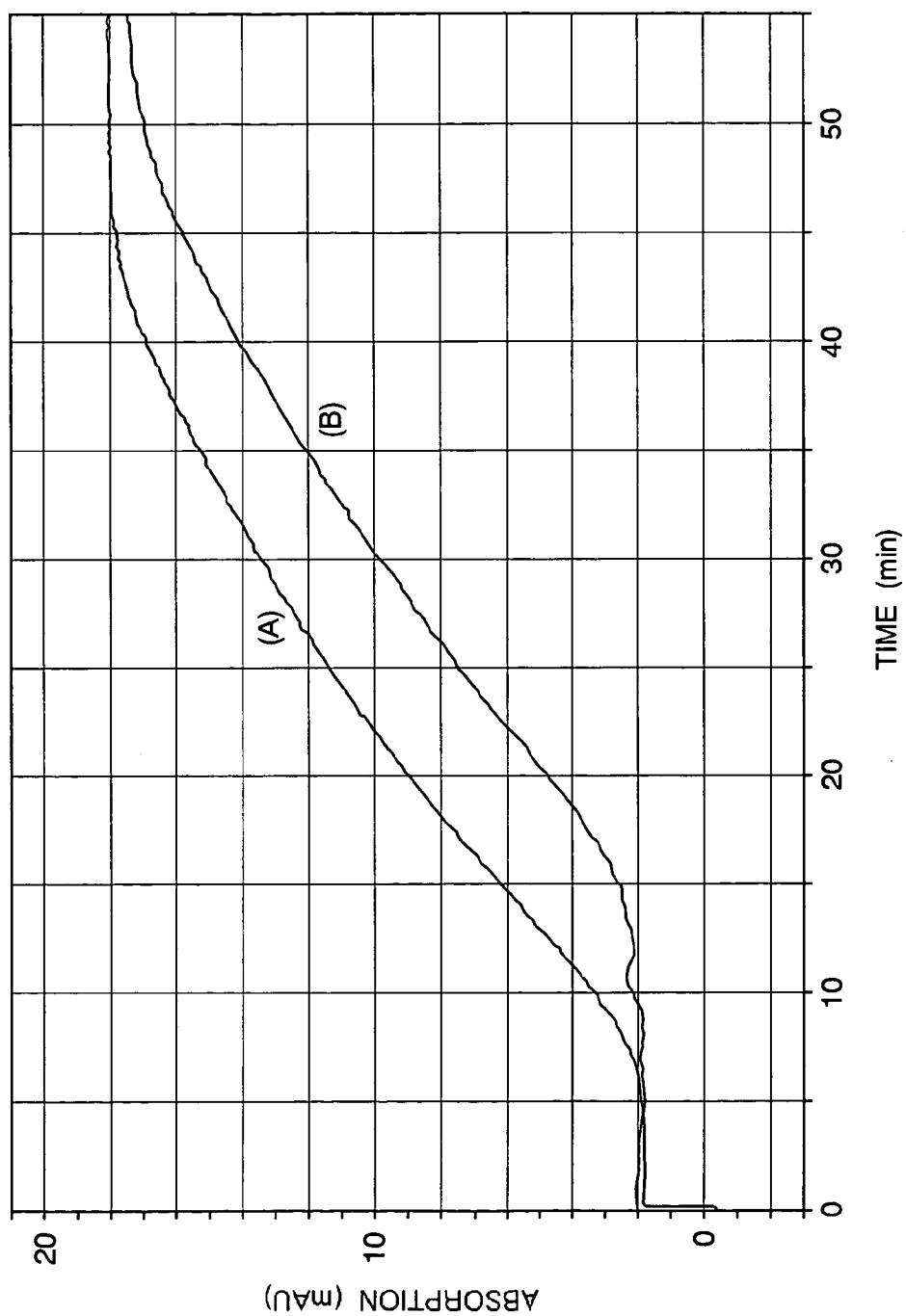
FIG. 3 is a drawing showing results that were obtained actually measured with respect to a gradient curve (continuous line) of a solution transferred by a pump 1 and a gradient curve (dotted line) of a solution transferred by the ten-ports valve.

FIG. 3 shows a nano-flow gradient curve obtained under the premise that a flow rate of the pump 2 is 500 nL/min., a flow rate of the pump 1 is 50 µL/min., and the ten-ports valve 3 is switched in every one minute. The liquids 6, 7 and 8 were water, an aqueous solution of 80% acetonitrile that contains 0.1% acetone, and water, respectively.

(A) is a gradient curve obtained by measuring change in light absorption (250 nm) of the solution wherein the UV light absorption detector is connected between the pump 1 and the ten-ports valve 3, and the pump 1 makes the solutions to be transferred to the ten-ports valve 3. (B) shows a gradient curve obtained by measuring a change in light absorption of the solution that is transferred to the separation column 14 wherein the UV light absorption detector is connected at the lower flow of the ten-ports valve 3. From the comparison between (A) and (B), it is seen that the gradient curve (B) having the good following property is obtained under the above-mentioned conditions.

The delay in rise of the gradient curve (B) is caused by delay in arriving time at the UV light absorption detector that is connected at the lower flow of the ten-ports valve 3, because the volume is so small as 500 nL/min.

In the present invention, it is possible to conduct continuous analysis, when the time program that is made by the gradient curve of the pump 1 starts in synchronizing with sample introduction by the sample injector. Since the volume of syringe of the pump 2 and an amount of the solution which is required for one analysis are calculated in advance, it is possible to control the controller 4 so as not to issue a start signal, when the pump 2 enters the aspiration operation. Further, it is possible to prevent fluctuation of the flow rate during analysis by using a pump that has a function of aspirating-compensation of the consumed solution in the column cleaning and equilibrium treatment period after one analysis is completed.

In general, in the gradient elution wherein the compositions of the organic solvents are changed as time goes, the column pressure may change due to a change in viscosity of the solutions. It is possible to make the minimum fluctuation at the time of switching of the ten-ports valve 3, when the pressure applied to the resistance coil 5 is kept at a similar level of pressure that is applied to the separation column. As a result, the fluctuation of flow rates caused by fluctuation of pressure applied to the separation column in one analysis can be minimized.

Further, it is possible to transfer solutions with a more stabilized nano-flow rate when the analyzer is placed as a whole in a constant temperature oven to keep the analyzer temperature constant.

Figure 4:
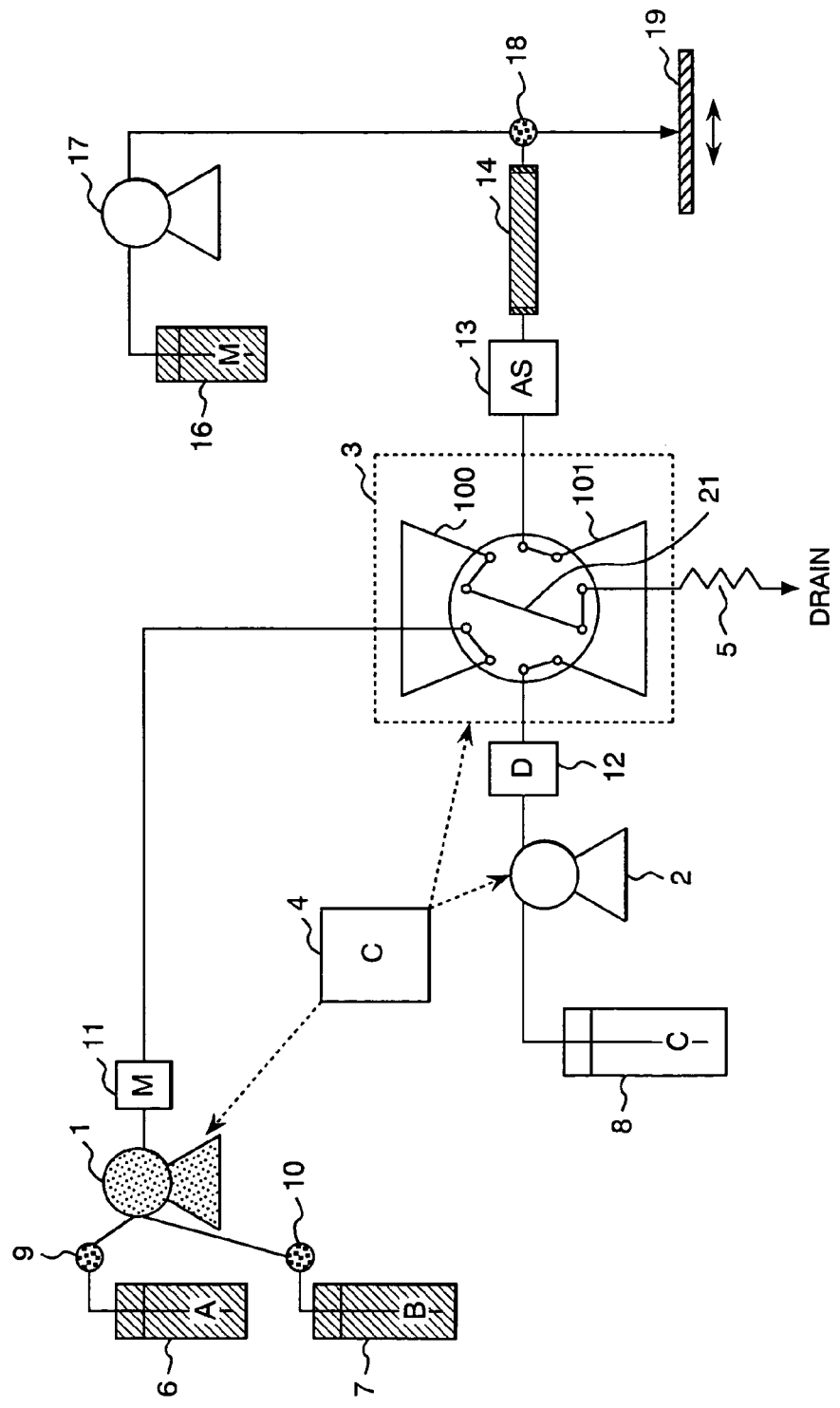
FIG. 4 is a diagrammatic drawing of another embodiment of the present invention.

FIG. 4 shows a diagrammatic view of another example of the present invention. The difference from FIG. 1 resides in the addition of means for pipetting. Since a flow rate eluted from the separation column 14 is a nano-flow level (nL/min.), such the small amount of discharged liquid does not make a liquid drop and it is very difficult to pipette the liquid. Thus, in this embodiment, a make-up solution 16 is combined with the solution from the separation column 14 with a make-up pump 17.

The flow rate of the make-up pump 17 is a micro flow level (µL/min.). The solution after combination is pipetted (divided) on a pipette plate 19. At this time, the pipette plate 19 is movable in both front and backward directions and right and left directions as well. In this embodiment, the flow rate of the eluted solution is a micro-flow level (µL/min.), so that the solution becomes liquid drops and pipetting is possible.

It is possible to use a solution wherein one or more of compounds that are suitable for matrix-laser dislocation ionized (MALDI) mass spectrometer.

Figure 5:
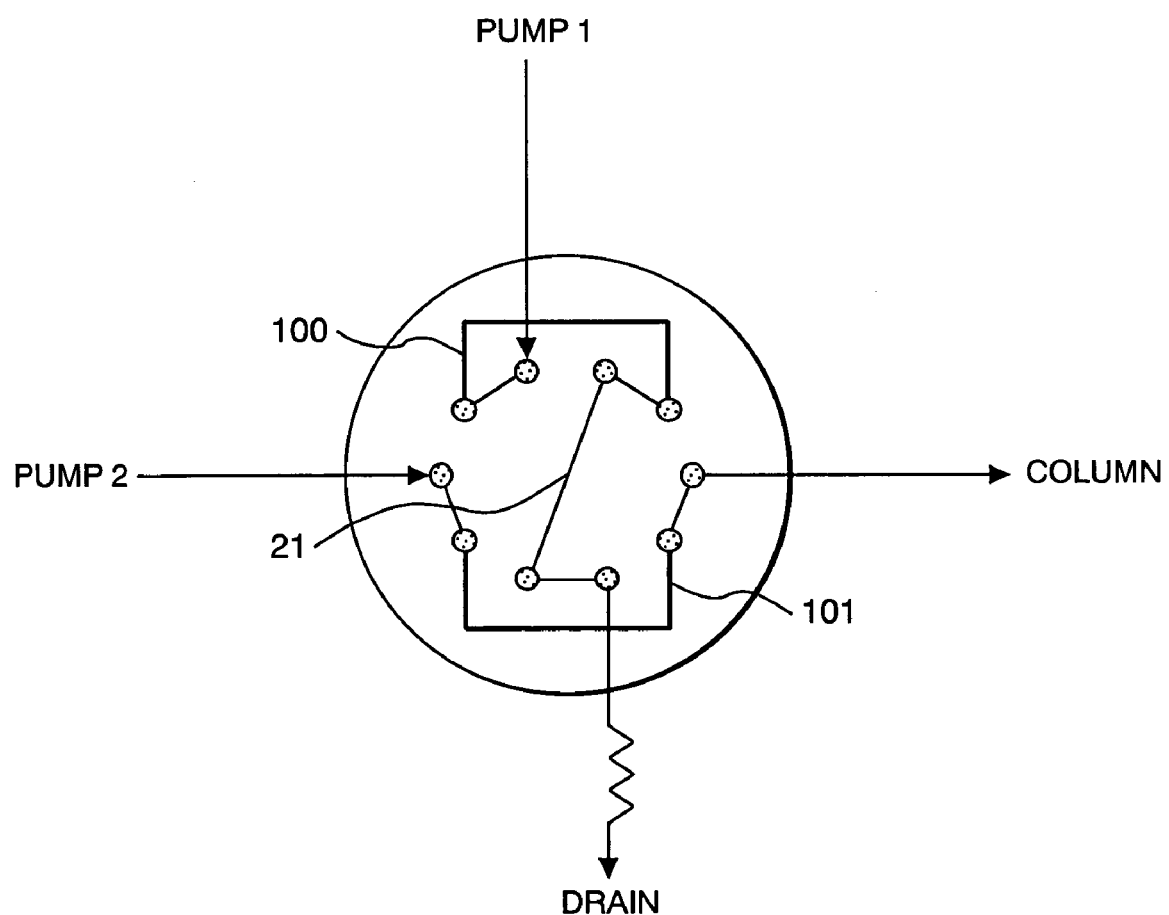
FIG. 5 is a flow chart of an improved ten-ports valve.

FIG. 5 and FIG. 6 show diagrammatic views of the improved ten-ports valves for the present invention. The ten-ports valve 3 comprises a rotary seal 22, a stator ring 25, a stator seal 24 and a stator, as shown in FIG. 6.

The thin continuous lines in the circle are grooves formed in the stator seal 24, the switching of the flow passages in the valve being carried out by rotation of this portion. On the other hand, the thick continuous lines, which are peculiar to this embodiment, are grooves formed in the stator 23. An ordinary ten-ports valve employs PEEK, SUS tubes, etc. for the sampling loops 100, 101 and flow passage 21. Since the volume of the sampling loops which deal with the nano-flow rate, about 1 micro-litter, the grooves (100, 101) in the stator can be used in place of the sampling loops. The flow passages 21 are the same as the sampling loops. As a result, six screw holes for connecting tubes can be eliminated, and connection of tubes becomes simple. The possibility that dust comes into at the time of tube connection job can be also eliminated.

According to the present invention, it is not necessary to prepare gradient solutions beforehand for each analysis. It is possible to carry out separation analysis with good reproducibility even at a flow rate of a nano-flow level (nL/min.) by gradient elution. Accordingly, it is possible to provide a liquid chromatography that is capable of continuous analysis for performing the gradient at a nano-flow level (nL/min.).

What is claimed is:

1. A separation analyzer comprising:
   a first pump for transferring liquid, while changing mixing ratios of plural kinds of solutions;
   a second pump for transferring a transfer solution;
   a sample introduction section;
   a separation column for separating a sample; and
   a detector for detecting the sample eluted from the separation column,
   wherein there is disposed a flow switching means having first and second sampling loops for temporarily storing the solutions and comprising a flow passage from the first pump, a flow passage from the second pump and a flow passage from the sample introduction section, the flow passages being connected with each other, and
   wherein the flow switching means alternatively assumes a first state where the second pump pushes out the solution in the second sample loop towards the sample introduction section, while transferring the solution from the first pump to the first sampling loop, and assumes a second state where the second pump pushes out the solution in the first sampling loop, towards the sample introduction section while transferring the solution from the first pump to the second sampling loop.

2. The separation analyzer according to claim 1, wherein the flow switching means has a discharge passage for discharging the solution outside of the analyzer, the passage having a flow resistance equivalent to that of the separation column, and wherein the first sampling loop is connected with the discharge passage in the first state, and the second sampling loop is connected with the discharge passage in the second state.

3. The separation analyzer according to claim 1 or 2, wherein the first pump transfers the solution at a rate of a micro-liter level (μL/min.) and the second pump transfers the solution at a rate of a nano-liter level (nL/mm.).

4. The separation analyzer according to claim 1, 2 or 3, wherein a volume of each of the first and second sampling loops is about 1 micro-liter (μL).

5. The separation analyzer according to claim 4, comprising a third pump for transferring the solution at a rate of a micro-liter level (μL/min.), a mixer for mixing the eluted solution from the separation column and the solution transferred from the third pump, and a pipetting section for pipetting the solution after the solutions are mixed by the mixer.

6. The separation analyzer according to claim 5, which further comprises a constant temperature oven for keeping the temperature of the analyzer constant.

7. The separation analyzer according to claim 2, wherein the flow switching means comprises a first member that comprises a first connection port to which the passage from the first pump is connected, a second connection port to which the passage from the second pump is connected, a third connection port to which the flow passage to the sample introduction section is connected, and a fourth connection port to which the discharge passage is connected, and a second member having a flow switching passage for switching between the first and second states, and wherein the first and second sampling loops are formed in the first and second members.

* * * * *